(12) United States Patent
Kelley

(10) Patent No.: US 8,066,726 B2
(45) Date of Patent: Nov. 29, 2011

(54) SERPENTINE CUTTING BLADE FOR CUTTING BALLOON

(75) Inventor: Greg S. Kelley, San Diego, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1522 days.

(21) Appl. No.: 10/996,099

(22) Filed: Nov. 23, 2004

(65) Prior Publication Data

US 2006/0111736 A1 May 25, 2006

(51) Int. Cl.
*A61B 17/22* (2006.01)
*A61D 1/02* (2006.01)
(52) U.S. Cl. ........................ 606/159; 606/194
(58) Field of Classification Search ............... 602/18; 606/159, 194; 623/1.11
See application file for complete search history.

(56) References Cited

U.S. PATENT DOCUMENTS

| | | | | |
|---|---|---|---|---|
| 2,102,069 A | * | 12/1937 | Hanicke | 602/18 |
| 3,220,406 A | * | 11/1965 | Connelly | 602/18 |
| 3,313,297 A | * | 4/1967 | Applegate et al. | 602/18 |
| 3,834,048 A | * | 9/1974 | Maurer | 36/50.1 |
| 4,273,128 A | | 6/1981 | Lary | 606/159 |
| 4,669,469 A | | 6/1987 | Gifford, III | 606/159 |
| 4,696,667 A | | 9/1987 | Masch | 604/22 |
| 4,728,319 A | | 3/1988 | Masch | 604/22 |
| 4,781,186 A | | 11/1988 | Simpson et al. | 606/171 |
| 4,784,636 A | | 11/1988 | Rydell | 604/22 |
| 4,787,388 A | | 11/1988 | Hofmann | 128/344 |
| 4,862,878 A | * | 9/1989 | Davison et al. | 602/20 |
| 4,867,157 A | | 9/1989 | McGurk-Burleson et al. | 606/170 |
| 4,886,061 A | | 12/1989 | Fischell et al. | 606/159 |
| 4,887,613 A | | 12/1989 | Farr et al. | 606/159 |
| 4,896,669 A | | 1/1990 | Bhate et al. | 606/194 |
| 4,909,781 A | | 3/1990 | Husted | 604/22 |
| 4,950,277 A | | 8/1990 | Farr | 606/159 |
| 4,963,313 A | | 10/1990 | Noddin et al. | 264/573 |
| 4,966,604 A | | 10/1990 | Reiss | 606/159 |
| 4,979,951 A | | 12/1990 | Simpson | 606/159 |
| 4,986,807 A | | 1/1991 | Farr | 604/22 |
| 5,005,563 A | * | 4/1991 | Veale | 602/18 |
| 5,030,201 A | | 7/1991 | Palestrant | 604/22 |
| 5,053,044 A | | 10/1991 | Mueller et al. | 606/159 |
| 5,071,424 A | * | 12/1991 | Reger | 606/159 |
| 5,074,871 A | | 12/1991 | Groshong | 606/170 |
| 5,091,205 A | | 2/1992 | Fan | 427/2 |
| 5,100,425 A | | 3/1992 | Fischell et al. | 606/159 |

(Continued)

FOREIGN PATENT DOCUMENTS

EP 0 565 799 B1 11/1992

(Continued)

OTHER PUBLICATIONS

U.S. Appl. No. 09/696,378, filed Oct. 25, 2000, Chen et al.

*Primary Examiner* — Gary Jackson
*Assistant Examiner* — Erin Colello
(74) *Attorney, Agent, or Firm* — Seager Tufte Wickhem LLC

(57) ABSTRACT

A system for treatment of a vessel lesion comprises an expandable balloon and at least one cutting blade engaged to an exterior surface of the balloon. At least a portion of the cutting blade has a substantially serpentine configuration defined by a plurality of interconnected peaks and troughs wherein each trough is in closer proximity to the balloon than each peak.

22 Claims, 14 Drawing Sheets

U.S. PATENT DOCUMENTS

| | | | | |
|---|---|---|---|---|
| 5,112,900 A | 5/1992 | Buddenhagen | | 524/484 |
| 5,156,610 A | 10/1992 | Reger | | 606/159 |
| 5,176,693 A | 1/1993 | Pannek, Jr. | | 606/159 |
| 5,178,625 A | 1/1993 | Groshong | | 606/159 |
| 5,181,920 A | 1/1993 | Mueller et al. | | 606/159 |
| 5,192,291 A | 3/1993 | Pannek, Jr. | | 606/159 |
| 5,196,024 A | 3/1993 | Barath | | 606/159 |
| 5,224,945 A | 7/1993 | Pannek, Jr. | | 606/159 |
| 5,226,887 A | 7/1993 | Farr et al. | | 604/103.09 |
| 5,226,909 A | 7/1993 | Evans et al. | | 606/159 |
| 5,250,059 A | 10/1993 | Andreas et al. | | 606/159 |
| 5,282,484 A | 2/1994 | Reger | | 128/898 |
| 5,320,634 A | 6/1994 | Vigil et al. | | 606/159 |
| 5,372,601 A | 12/1994 | Lary | | 606/159 |
| 5,447,497 A | 9/1995 | Sogard et al. | | 604/101.02 |
| 5,527,325 A | 6/1996 | Conley et al. | | 606/159 |
| 5,556,408 A | 9/1996 | Farhat | | 606/180 |
| 5,616,149 A | 4/1997 | Barath | | 606/159 |
| 5,669,920 A | 9/1997 | Conley et al. | | 606/159 |
| 5,688,229 A * | 11/1997 | Bauer | | 602/18 |
| 5,697,944 A | 12/1997 | Lary | | 606/159 |
| 5,713,913 A | 2/1998 | Lary et al. | | 606/159 |
| 5,718,684 A | 2/1998 | Gupta | | 604/103.07 |
| 5,728,123 A | 3/1998 | Lemelson et al. | | 604/22 |
| 5,766,203 A | 6/1998 | Imran et al. | | 623/1.11 |
| 5,792,158 A | 8/1998 | Lary | | 606/159 |
| 5,797,935 A | 8/1998 | Barath | | 606/159 |
| 5,800,450 A | 9/1998 | Lary et al. | | 606/180 |
| 5,833,657 A | 11/1998 | Reinhardt et al. | | 604/96 |
| 5,919,200 A | 7/1999 | Stambaugh et al. | | 606/159 |
| 6,001,112 A | 12/1999 | Taylor | | 606/159 |
| 6,036,708 A | 3/2000 | Sciver | | 606/159 |
| 6,117,153 A | 9/2000 | Lary et al. | | 606/170 |
| 6,165,187 A | 12/2000 | Reger | | 606/159 |
| 6,254,560 B1 * | 7/2001 | Tweardy et al. | | 602/18 |
| 6,258,108 B1 | 7/2001 | Lary | | 606/159 |
| 6,306,151 B1 | 10/2001 | Lary | | 606/159 |
| 6,398,798 B2 | 6/2002 | Selmon et al. | | 606/159 |
| 6,416,523 B1 | 7/2002 | Lafontaine | | 606/159 |
| 6,428,552 B1 | 8/2002 | Sparks | | 606/159 |
| 6,447,468 B1 * | 9/2002 | Hankins et al. | | 602/18 |
| 6,494,854 B1 * | 12/2002 | Visness et al. | | 602/18 |
| 6,517,514 B1 | 2/2003 | Campbell | | 604/96.01 |
| 6,562,062 B2 | 5/2003 | Jenusaitis et al. | | 623/1.11 |
| 6,565,527 B1 | 5/2003 | Jonkman et al. | | 604/96.01 |
| 6,632,231 B2 | 10/2003 | Radisch, Jr. | | 606/159 |
| 6,685,718 B1 | 2/2004 | Wyzgala et al. | | 606/170 |
| 6,730,105 B2 | 5/2004 | Shiber | | 606/159 |
| 7,686,824 B2 * | 3/2010 | Konstantino et al. | | 606/194 |
| 7,691,119 B2 * | 4/2010 | Farnan | | 606/194 |
| 2002/0010489 A1 * | 1/2002 | Grayzel et al. | | 606/194 |
| 2002/0151924 A1 | 10/2002 | Shiber | | 606/194 |
| 2003/0078606 A1 * | 4/2003 | Lafontaine et al. | | 606/159 |
| 2003/0144677 A1 | 7/2003 | Lary | | 606/159 |
| 2003/0144683 A1 * | 7/2003 | Sirhan et al. | | 606/194 |
| 2003/0153870 A1 * | 8/2003 | Meyer et al. | | 604/96.01 |
| 2003/0163148 A1 | 8/2003 | Wang et al. | | 606/159 |
| 2004/0034384 A1 * | 2/2004 | Fukaya | | 606/191 |
| 2004/0098014 A1 * | 5/2004 | Flugelman et al. | | 606/192 |
| 2004/0122457 A1 | 6/2004 | Weber | | 606/159 |
| 2004/0127920 A1 | 7/2004 | Radisch, Jr. | | 606/159 |
| 2005/0240148 A1 * | 10/2005 | Cheves et al. | | 604/103.08 |

FOREIGN PATENT DOCUMENTS

WO            01/87372        11/2001

* cited by examiner

A-A

B-B

D-D

E-E

F-F

H-H

SERPENTINE CUTTING BLADE FOR CUTTING BALLOON

CROSS-REFERENCE TO RELATED APPLICATIONS

Not Applicable

STATEMENT REGARDING FEDERALLY SPONSORED RESEARCH

Not Applicable

BACKGROUND OF THE INVENTION

Arterial blockages, which are also called stenosis, lesions, stenotic lesions, etc, are typically caused by the build-up of atherosclerotic plaque on the inside wall of an artery. In fact, several such stenoses may occur contiguously within a single artery. This can result in a partial, or even complete, blockage of the artery. As a result of the danger associated with such a blockage, several methods and procedures have been developed to treat stenoses. One such method is an angioplasty procedure which uses an inflatable balloon to dilate the blocked artery. A typical inflatable angioplasty device, for example, is disclosed in U.S. Pat. No. 4,896,669.

Angioplasty balloons have enjoyed widespread acceptance in the treatment of stenoses. Recent studies, however, have indicated that the efficacy of the dilation of a stenosis is enhanced by first, or simultaneously, incising the material that is creating the stenosis. Consequently, recent developments have been made to equip angioplasty balloons with cutting edges, or atherotomes, which are intended to incise a stenosis during the dilation procedure. For example, U.S. Pat. Nos. 5,196,024; 5,616,149 and 5,797,935, the entire contents of each of which are incorporated herein by reference, respectively describe an inflatable angioplasty balloon having a number of atherotomes mounted longitudinally on the surface of the balloon. Upon inflation of the balloon, the atherotomes induce a series of longitudinal cuts into the surface of the stenotic material as the balloon expands to dilate the stenosis. As a result of such cuts, the stenosis is more easily dilated, and the likelihood of damaging the artery during dilation is reduced.

Blades in many existing cutting balloon assemblies tend to be fairly rigid, particularly in the axial direction. The rigid axial structure of the blade naturally limits the blades ability to elongate with the underlying balloon material during balloon expansion at high pressure. As a result, stress between the comparatively axially rigid blade and the elongating balloon may lead to stress therebetween. This stress can lead to de-lamination of the blade and/or adhesive from the balloon. The effect of balloon elongation is more pronounced in larger diameter balloons than in smaller diameter balloons, and is further amplified in longer balloon lengths as well. As such, it has been necessary, particularly in larger vessel applications, to limit the materials of blade equipped balloons to those that are fairly stiff such as PET, PEN, etc. in order to minimize axial elongation.

Existing blades also tend to be fairly rigid in the transverse direction as well. This has the affect of limiting the flexibility of the balloon as it is advanced through the tortuous confines of a vessel or other body lumen.

In light of the above it would be desirable to provide a cutting blade for use with a cutting balloon that is more flexible, and which does not interfere with or is compatible with the expansion characteristics of the balloon to which it may be mounted.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

The present invention is directed to several embodiments. In at least one embodiment the invention is directed to a medical balloon for use with a catheter or similar device, wherein the medical balloon is equipped with at least one cutting blade.

In some embodiments one or more portions of the cutting blade or blades define a serpentine path or shape relative to the surface of the balloon upon which the blade is mounted. A serpentine path extends radially outward from the balloon surface and then back toward the balloon surface in a repeating pattern.

In at least one embodiment the serpentine path is provided by a plurality of adjacent undulations. In at least one embodiment adjacent undulations define a substantially S-shaped segment of the blade.

In at least one embodiment the blade has multiple serpentine regions, each of which define a separate serpentine path. Each serpentine region is separated by a region of the blade which is not serpentine. The non-serpentine regions may be characterized as being linear, and while such regions may define a path having one or more bends or curves to accommodate the shape of the balloon (e.g. the transition form the balloon waist to the balloon cone, the transition from the balloon cone to the balloon body, etc.) such regions do not define a serpentine path.

In some embodiments the blade employs separate serpentine regions each of which extend along the surface of a balloon cone, and a serpentine region which extends along the surface of at least a portion of the balloon body. Such cone serpentine regions of the blades and the body serpentine regions of the blade may have similar or different serpentine shapes or pathways. For example, in at least one embodiment, the cone serpentine regions define a path having a shallower height and/or a longer wavelength than the body serpentine region.

The blade may be constructed of any material suitable for forming a cutting blade. The body region of the blade defines at least one cutting surface or edge. Regions of the blade adjacent to the body region need not include a cutting surface. As such, in at least one embodiment different regions of the blade define one or more different cross-sectional shapes. In at least one embodiment the body region of the blade defines a substantially triangular shaped cross-section. In at least one embodiment regions of the blade adjacent the body region have rectangular (ribbon), round, ovoid, square or other cross-sectional shape(s).

In at least one embodiment one or more portions of the blade in close proximity to the balloon surface are engaged to the balloon surface by an adhesive or other mounting material. The adhesive may be any adhesive material suitable for securing a metal, polymer or carbon based blade to the material of the balloon.

In at least one embodiment portions of the blade engaged to the balloon are defined by the "troughs" of the serpentine path of the body region of the blade. Adjacent "peaks" are then free to flex, bend, or otherwise alter their position as the balloon is expanded, bent or otherwise altered in shape or configuration. This substantial freedom of movement of the peak portions of the body region allow the blade to remain in contact with the balloon regardless of the balloon's longitudinal expansion or axially transverse bending. In some embodiments the proximal and distal end regions of the blade, which respectively extend over the proximal and distal waists of the balloon are likewise engaged to the balloon and/or adjacent catheter shaft with an adhesive or mounting material. In some embodiments the blade ends are encased in adhesive or mounting material to prevent contact of the blade ends with the lumen wall through which the catheter is advanced.

As indicated above, a balloon may be equipped with any number of blades as desired. In at least one embodiment for example, the balloon is provided with a single blade, while in other embodiments 2-20 blades may be mounted onto the balloon. Multiple blades may be uniformly or irregularly spaced apart, and may have similar or different shapes, lengths, serpentine paths, etc.

These and other embodiments which characterize the invention are pointed out with particularity in the claims annexed hereto and forming a part hereof. However, for further understanding of the invention, its advantages and objectives obtained by its use, reference should be made to the drawings which form a further part hereof and the accompanying descriptive matter, in which there is illustrated and described a embodiments of the invention.

BRIEF DESCRIPTION OF THE SEVERAL VIEWS OF THE DRAWING(S)

A detailed description of the invention is hereafter described with specific reference being made to the drawings.

DETAILED DESCRIPTION OF THE INVENTION

Figure 1:
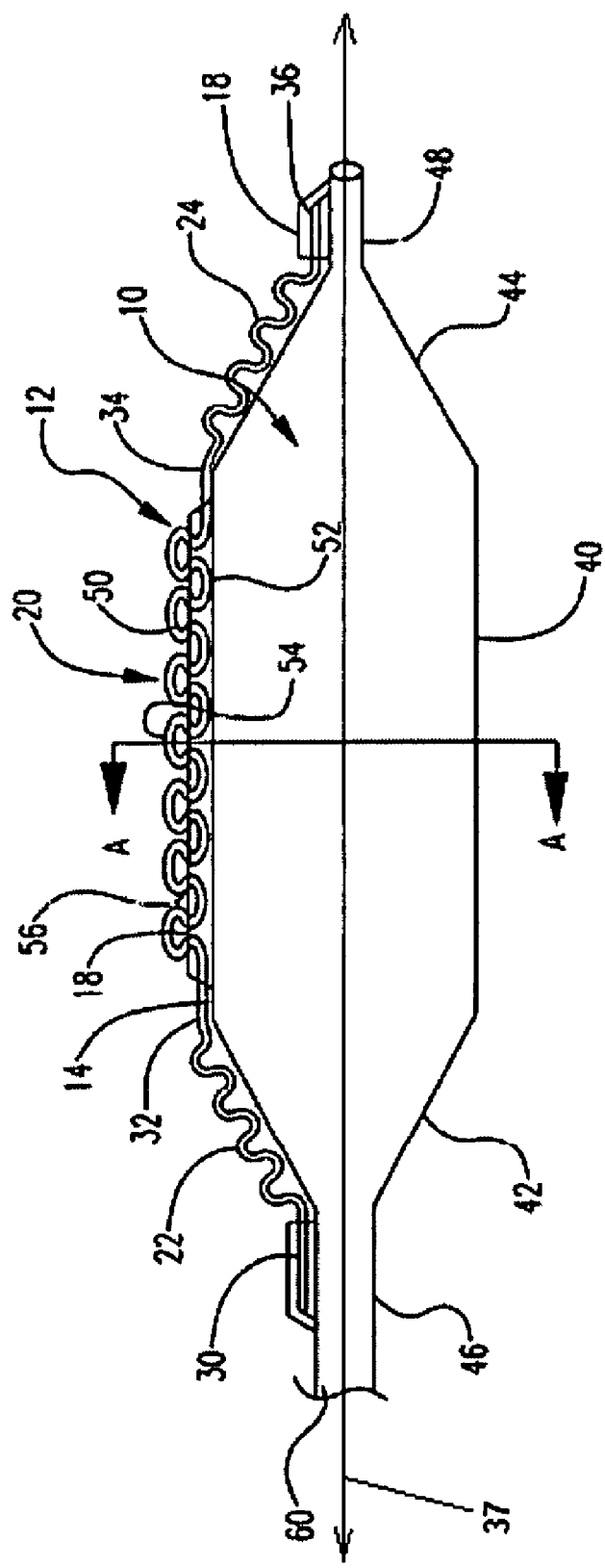
FIG. 1 is a side view of an embodiment of the invention wherein a balloon is shown with a single serpentine blade.

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

As indicated above, the present invention is embodied in a variety of forms.

In at least one embodiment, an example of which is depicted in FIG. 1, the invention is directed to a catheter balloon 10 which has at least one serpentine, undulating, or similarly configured blade 12 mounted to the external surface 14 of the balloon. As shown, the blade 12 comprises at least one serpentine region 20. The majority or all of the blade may have a serpentine configuration, the blade may comprise a single serpentine region or any number of serpentine regions separated by non-serpentine regions. In the example shown in FIG. 1, the blade 12 may be characterized as having a number of adjacent serpentine regions: body region 20, proximal cone region 22 and distal cone region 24; as well as one or more linear or non-serpentine regions: proximal end region 30, proximal cone transition region 32, distal cone transition region 34, and distal end region 36. The blade 12 extends substantially parallel to longitudinal axis 37 of the balloon 10.

Figure 13:
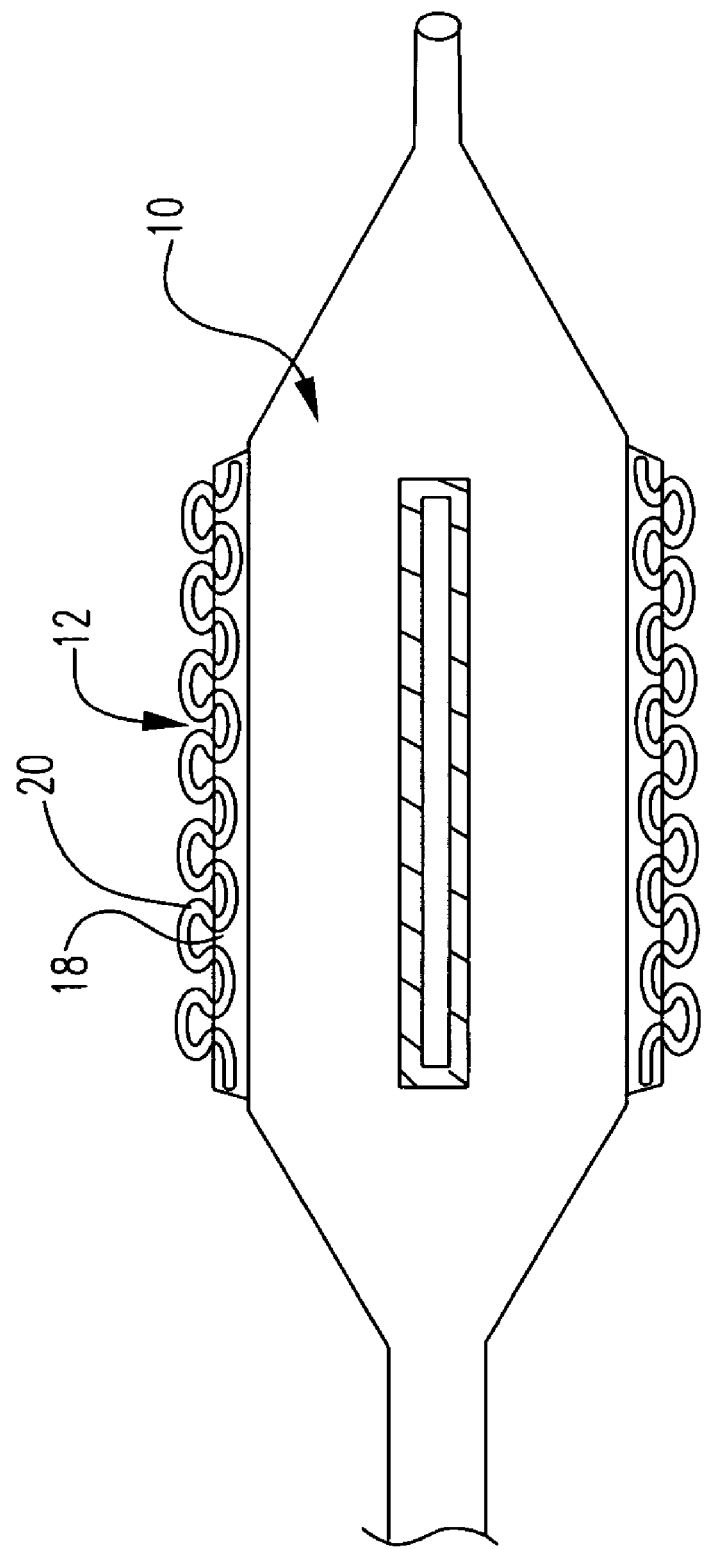
FIG. 13 is a side view of the embodiment shown in FIG. 1 wherein the serpentine blades are positioned on the body or working portion of the balloon.

In an alternative embodiment depicted in FIG. 13, each blade 12 is in effect a body region 20 having an uninterrupted serpentine configuration extending along at least a portion of only the balloon body 40.

As is shown in FIG. 1 and FIG. 13 the body serpentine region 20 extends along the exterior surface 14 of at least a portion of the balloon body 40. The body region 20 may be engaged to the balloon body 40 in any of a variety of ways such as by mechanical engagement, direct welding, through the use of an adhesive, etc. In the embodiment shown an adhesive material 18 is positioned on the surface 14 of the balloon 10 and the body region 20 of the blade 12 is adhesively engaged thereto.

Any suitable adhesive may be utilized as the adhesive material 18. For example adhesives such as polyurethane, epoxy, cyanoacrylate and/or combinations of such materials may by utilized as the adhesive material 18. In at least one embodiment, portions of the blade 12 are adhesively engaged to the balloon surface with a polyurethane substrate or pad such as is described in U.S. Pat. No. 5,320,634, the entire contents of which being incorporated herein by reference.

The nature of the serpentine regions 20, 22, 24 of the blade 12 is such that each serpentine region comprises a series of adjacent substantially S-shaped segments 50 (highlighted) which extend from a low point or trough 52, immediately adjacent to the surface 14 of the balloon 10, to a high point or peak 54, which is a greater distance radially outward from the balloon 10 than the trough 52.

Adjacent peaks 54 and troughs 52 are engaged by arm portions 56 of the blade 12. Each trough 52 is engaged to the balloon surface 14 by the adhesive material 18. The arm portions extend from the ends of the troughs 52 to engage the adjacent peaks 54. The arms 56 provide the peaks 54 with a significant degree of axial and transverse flexibility relative to the troughs 52 engaged to the balloon 10. As a result, when the balloon is twisted, bent, expanded or lengthened, stress between the blade 12 and the balloon 10 is minimized as the majority of the body serpentine region 20 remains free to move in conjunction/response with the movements of the balloon, while only the discrete and separated troughs 52 remain secured to the balloon 10.

Such a configuration provides the cutting balloon 10 with improved resistance to delamination of the blade 12 from the balloon surface 14 by reducing the axial and transverse stress that the balloon/blade interface is subjected to during expansion and/or movement of the balloon.

In some embodiments where the blade(s) 12 extend beyond the length of the balloon body 40, such as is shown in FIGS. 1-5, one or more blades 12 may be provided with cone regions 22 and 24 which also have a serpentine configuration. The cone regions 22 and 24 can be configured such that they elongate during balloon inflation resulting in a tension within the cone regions. Such tension will facilitate a desirable balloon refold, because during balloon deflation the cone region tension will preferentially draw in the blades 12 to a lower profile than the adjacent balloon folds. The serpentine configuration of the cone regions 22 and 24 provide additional flexibility, particularly in the axial direction, which allows the blade to accommodate expansion and/or elongation of the cones 42 and 44, respectively, as the balloon 10 is expanded without affecting the position or exerting axial stress on the body region 20 of the blade 12.

In order to minimize profile and to aid in balloon folding/refolding, in some embodiments the cone regions 22 and 24 are spaced apart or separated from the body region 20 by a non-serpentine cone transition region 32 and 34. In other embodiments regions 32 and 34 may be serpentine, linear, or provided with any other configuration desired.

In at least one embodiment the transition regions 32 and 34 as well as the serpentine cone regions 22 and 24 are not adhesively or otherwise engaged to the balloon surface 14. By not adhering the respective regions to the balloon, the blade 12 is more readily able to accommodate much greater degrees of change in the shape and configuration of the balloon without placing stress on the body region 20.

The end regions, proximal end region 30 and distal end region 36 are also typically non-serpentine in configuration, in order to minimize their profile and to provide greater surface area for engagement to the balloon waists (proximal waist 46 and distal waist 48) respectively thereunder. In some embodiments the end regions 30 and 36 may be configured to extend beyond the waists 46 and 48 and engage the catheter shaft 60 directly.

In at least one embodiment, at least a portion of each end region 30 and 36 of the blade 12, is completely encased or enclosed by adhesive or other mounting material upon or within the respective waist of the balloon 10 or catheter shaft 60.

Figure 2:
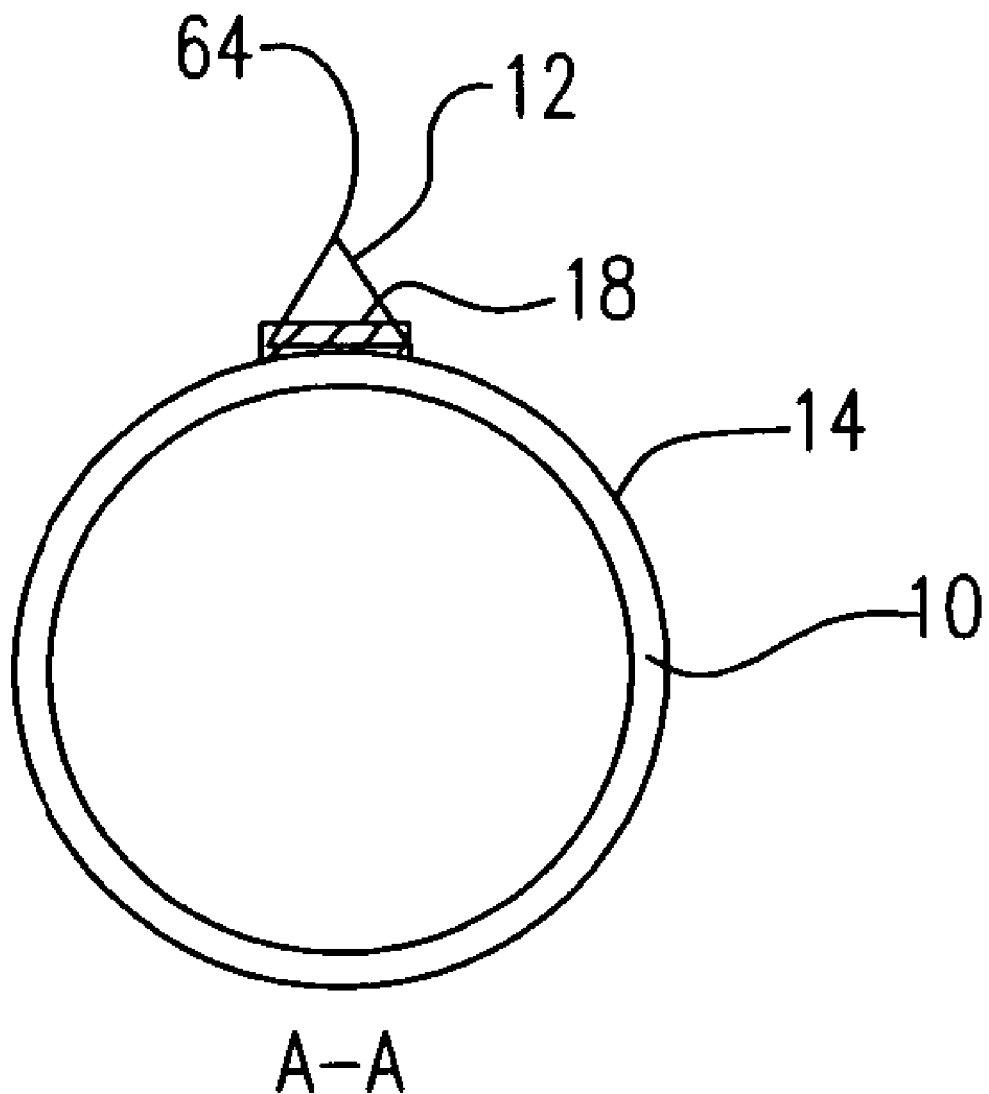
FIG. 2 is a cross-sectional view of the embodiment depicted in FIG. 1.
Figure 3:
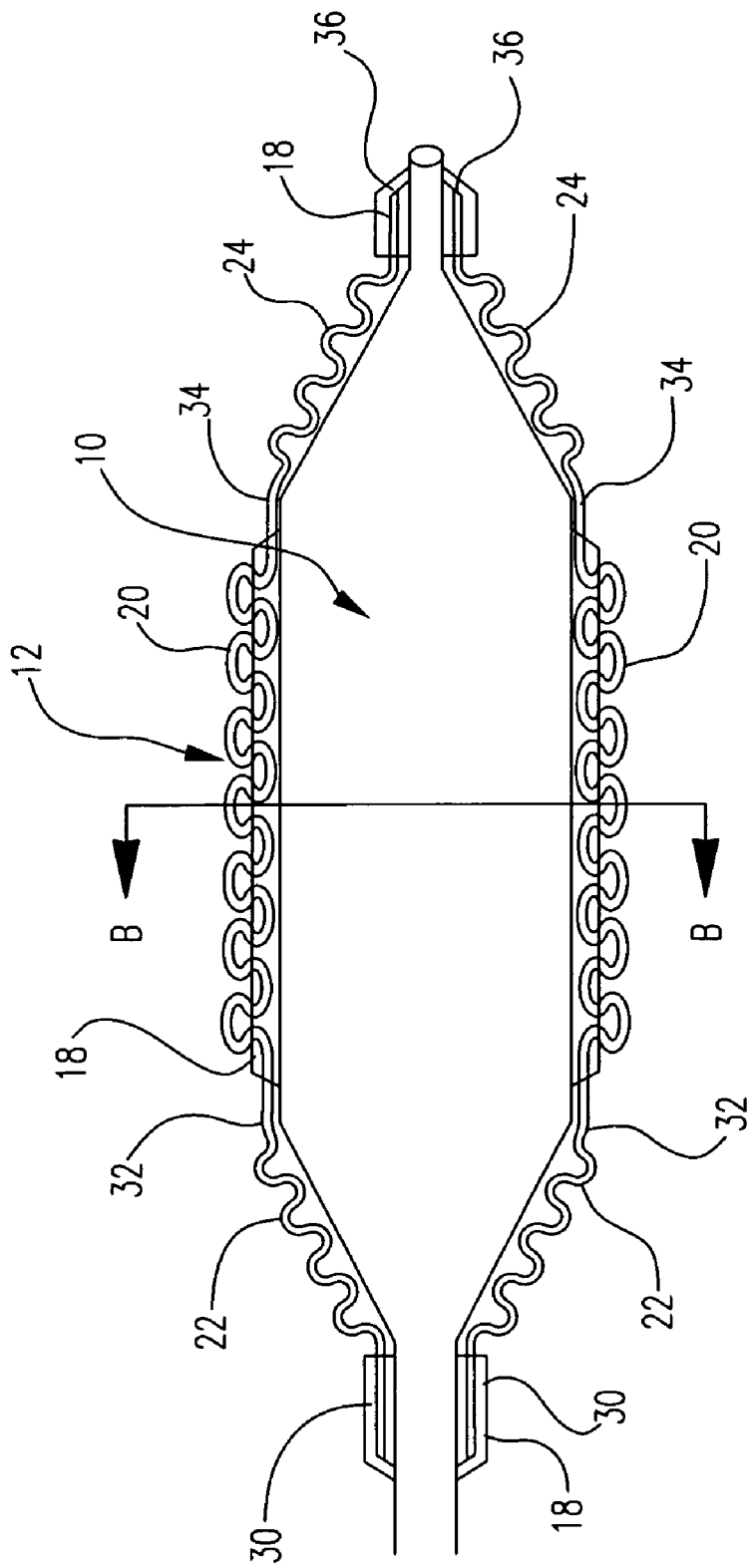
FIG. 3 is a side view of the embodiment shown in FIG. 1 wherein the balloon includes 2 serpentine blades.
Figure 4:
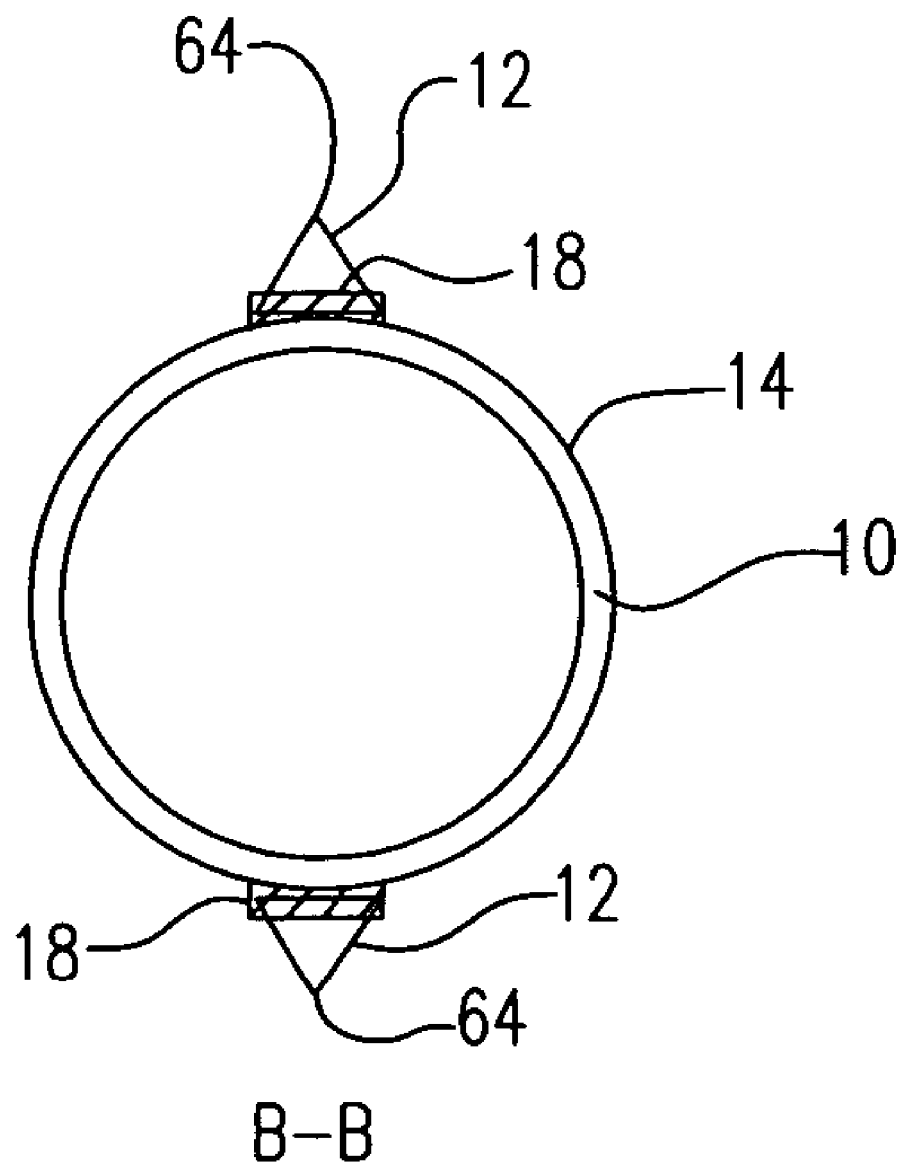
FIG. 4 is a cross-sectional view of the balloon shown in FIG. 3
Figure 5:
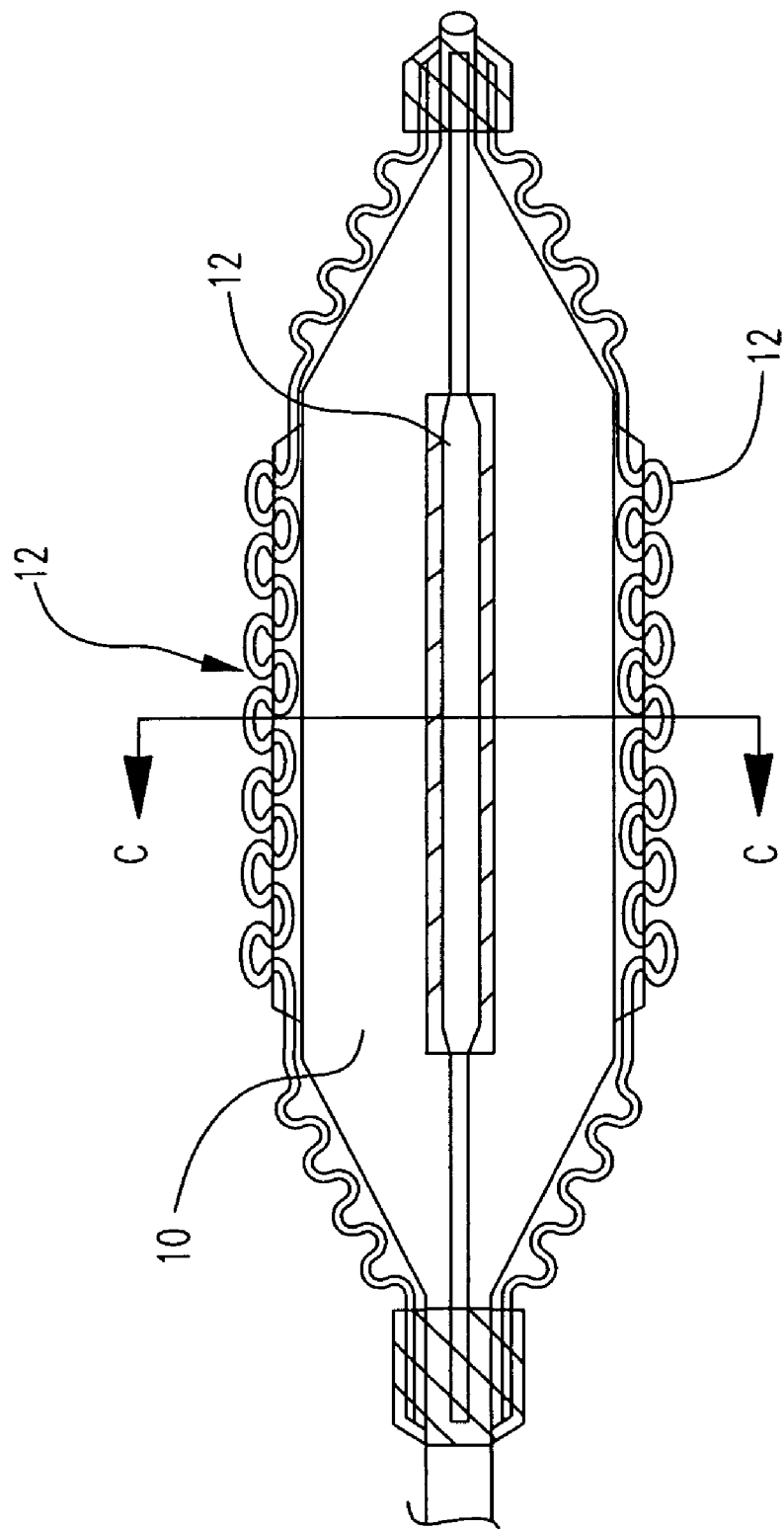
FIG. 5 is a side view of the embodiment shown in FIG. 1 wherein the balloon includes 4 serpentine blades.
Figure 6:
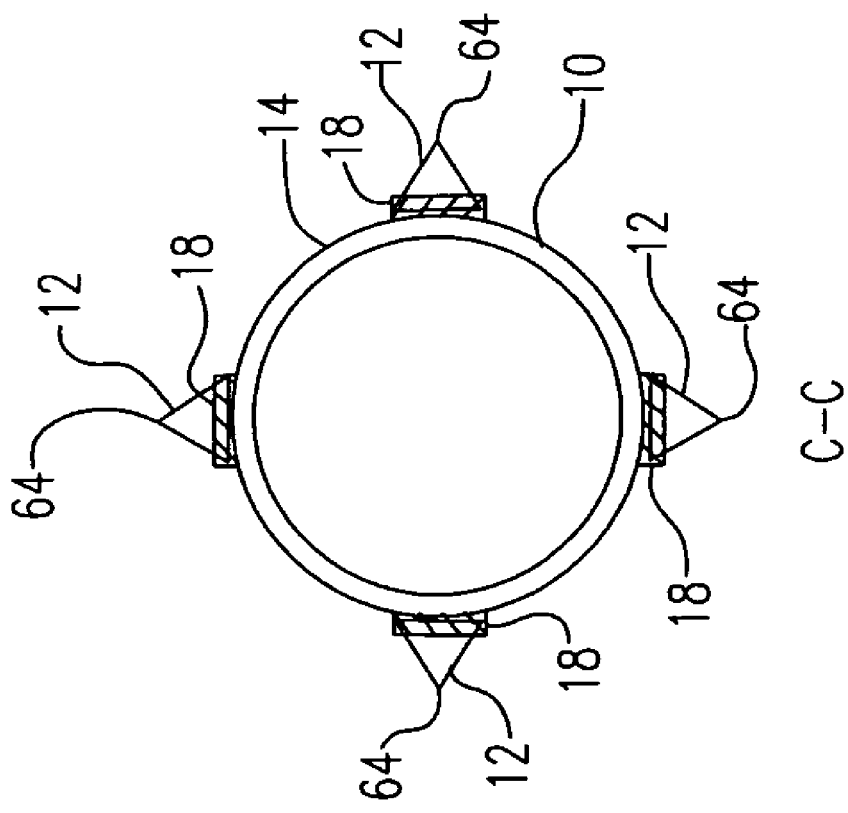
FIG. 6 is a cross-sectional view of the balloon shown in FIG. 5

As is illustrated in FIGS. 1-6, the balloon 10 may be equipped with any number of blades 12, typically between 1 and 20, though other numbers may be provided. In FIGS. 1-2 for example, the balloon 10 is shown with a single blade 12. In the embodiment shown in FIGS. 3-4, the balloon 10 is provided with a pair of radially opposite blades 12. In FIGS. 5-6, the balloon is provided with four substantially circumferentially equidistant blades 12.

While the embodiments shown in FIGS. 2-6 have blades 12 arranged in a symmetrical fashion about the balloon 10, such symmetry need not be the case in all embodiments. In some embodiments the blades may be of different or equal lengths; varyingly spaced apart, whether randomly or in accordance with a pattern; or otherwise arranged or positioned about the balloon in accordance with need, desire and/or performance.

Figure 7:
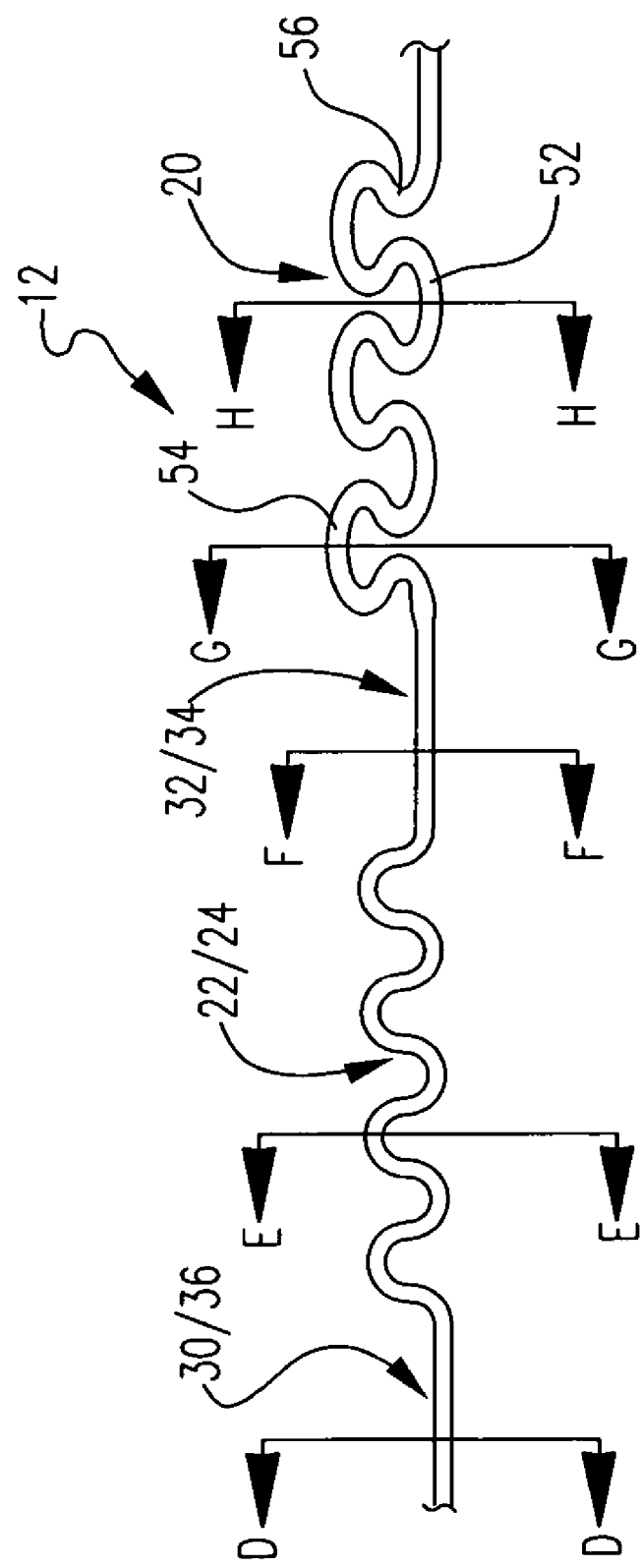
FIG. 7 is a detailed side view of a serpentine blade such as is shown in FIGS. 1-6.
Figure 11:
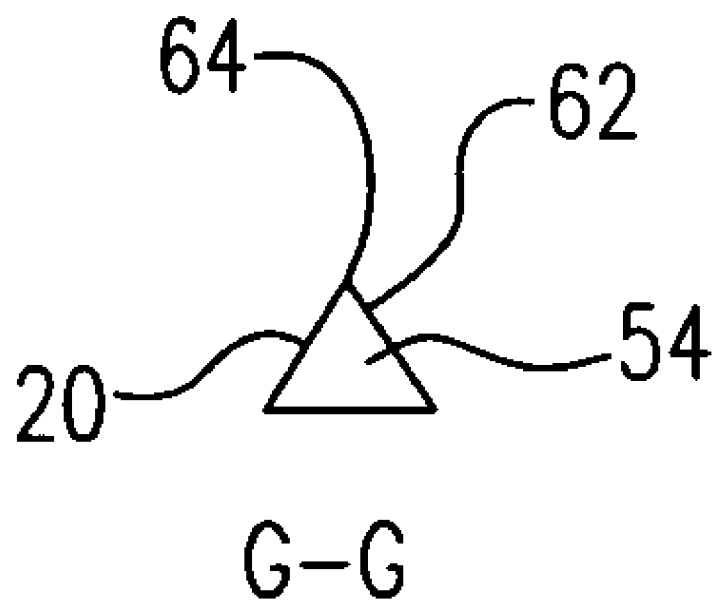
Figure 12:
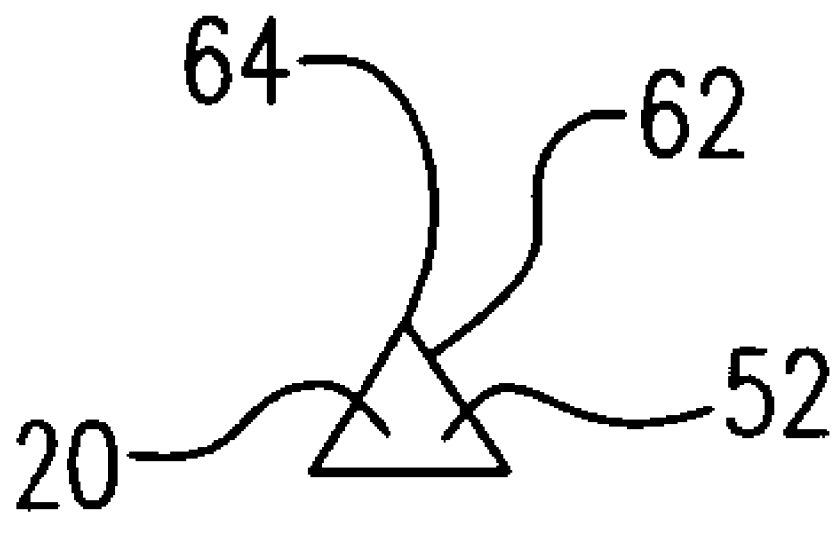

As is the nature of a "cutting blade" one or more portions of the surface 62 of the blade 12 define one or more cutting edges. In the various embodiments shown herein at least the peak portions 54 of the body region 20 define a single radially outward projecting cutting edge 64. As is illustrated in FIG. 7 and in the cross-sectional views provided in FIGS. 11 and 12 the cutting edge 64 can be formed within the body region 20 with a substantially triangular cross-sectional shape, wherein the edge 64 is formed by the peak or apex 64 of the triangular shaped blade. While it is desired to provide at least the peaks 54 with an edge, in at least one embodiment, as illustrated in FIG. 12, the troughs 52 may also be provided with an edge 64 as a consequence of the triangular cross-sectional shape of the region 20.

In the embodiments depicted in FIGS. 1-12, the portions of the blade 12 adjacent to the body region 20 of the blade need not be provided with an edge, (as such portions are typically not positioned in such a manner so as to contact a lesion site). In some embodiments, those regions of the blade other than the body region 20 (e.g. regions 22, 24, 30, 32, 34 and 36) of the blade 12 can be configured with a cross-sectional shape different than that of the body region 20.

Figure 8:
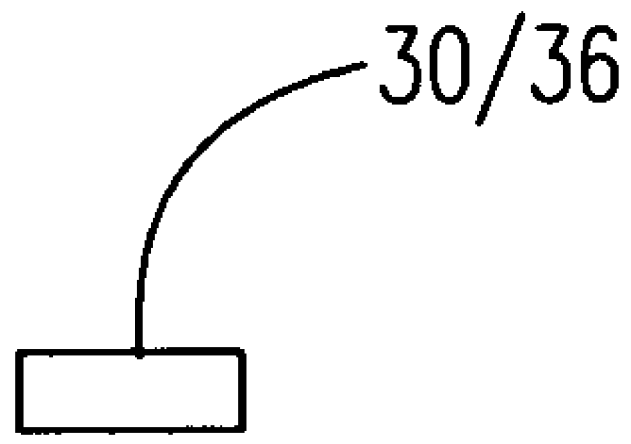
FIGS. 8-12 are each cross-sectional views of respective portions of the blade shown in FIG. 7.
Figure 9:
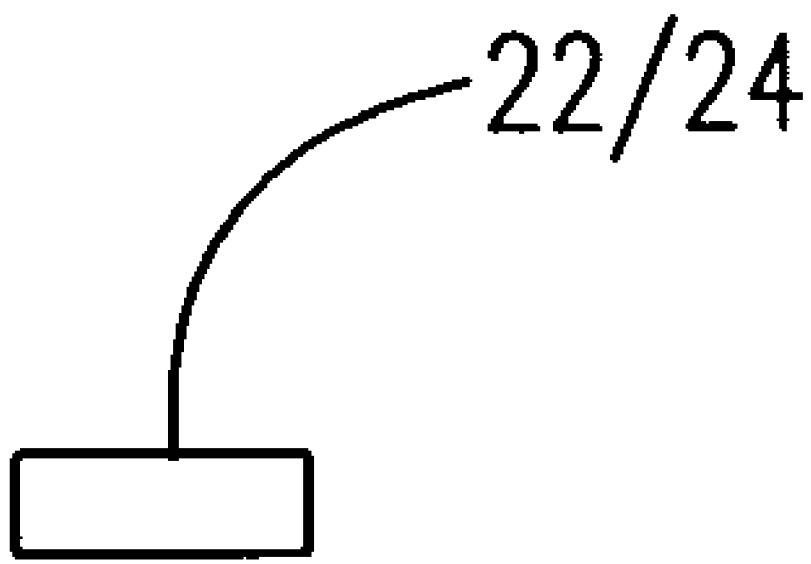
Figure 10:
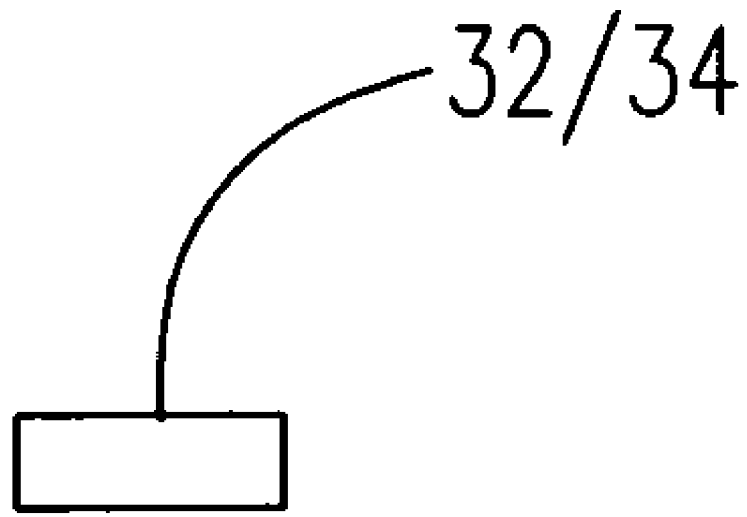

For example, as illustrated in FIGS. 7-10, the regions 22/24, 30/36, 32/34 adjacent to the body region 20 are provided with comparatively thin, or ribbon-like cross-sectional shape, as shown in FIGS. 8-10, which provides those portions of the blade adjacent to the body region 20 with a high degree of axial and/or transverse flexibility. It should be understood that the ribbon-like shape shown in FIGS. 8-10 is an example of a desired shape, others include but are not limited to, round, ovoid, ellipsoid, square, triangular, or any other geometric shape that may be desired.

The blade 12, regardless of its cross-sectional shape or shapes may be constructed by any of a variety of manufacturing methods. For example, the blade 12, or at least the body region 20 may be constructed of metallic or other material wire stock, as it will facilitate the formation of the cutting edge. Other manufacturing techniques include photo-etching, laser cutting, water jet cutting, or flat stock stamping of a desired blade material to form one or more regions of the blade 12.

In some embodiments the blade 12 or one or more portions thereof may include one or more areas, coatings, materials, etc. that is (are) detectable by imaging modalities such as X-Ray, MRI or ultrasound. In some embodiments at least a portion of the blade is at least partially radiopaque.

In at least one embodiment, the blade 12, and/or the balloon 10 may be configured to deliver one or more therapeutic agents to the lesion site. A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof. Where the therapeutic agent includes a polymer agent, the polymer agent may be a polystyrene-polyisobutylene-polystyrene triblock copolymer (SIBS), polyethylene oxide, silicone rubber and/or any other suitable substrate.

Blade 12, may be constructed from one or more metals, polymers, combinations of one or more metals and/or polymers, and/or other desired material(s). In at least one embodiment, blade 12 is at least partially constructed of a shape memory material, such as nitinol and/or a shape memory polymer. The blade 12, may comprise a plurality of separate blade segments or may be a single continuous structure as desired.

The balloon 10 may be made of any suitable balloon material including compliant and non-compliant materials and combinations thereof. Some examples of suitable materials for constructing the balloon 10 include but are not limited to: low pressure, relatively soft or flexible polymeric materials, such as thermoplastic polymers, thermoplastic elastomers, polyethylene (high density, low density, intermediate density, linear low density), various co-polymers and blends of polyethylene, ionomers, polyesters, polyurethanes, polycarbonates, polyamides, poly-vinyl chloride, acrylonitrile-butadiene-styrene copolymers, polyether-polyester copolymers, and polyetherpolyamide copolymers; copolymer polyolefin material available from E.I. DuPont de Nemours and Co. (Wilmington, Del.), under the trade name Surlyn™; ionomer and a polyether block amide available under the trade name PEBAX™; high pressure polymeric materials, such as thermoplastic polymers and thermoset polymeric materials, poly (ethylene terephthalate) (commonly referred to as PET), polyimide, thermoplastic polyamide, polyamides, polyesters, polycarbonates, polyphenylene sulfides, polypropylene and rigid polyurethane; one or more liquid crystal polymers; and combinations of one or more of any of the above.

Figure 14:
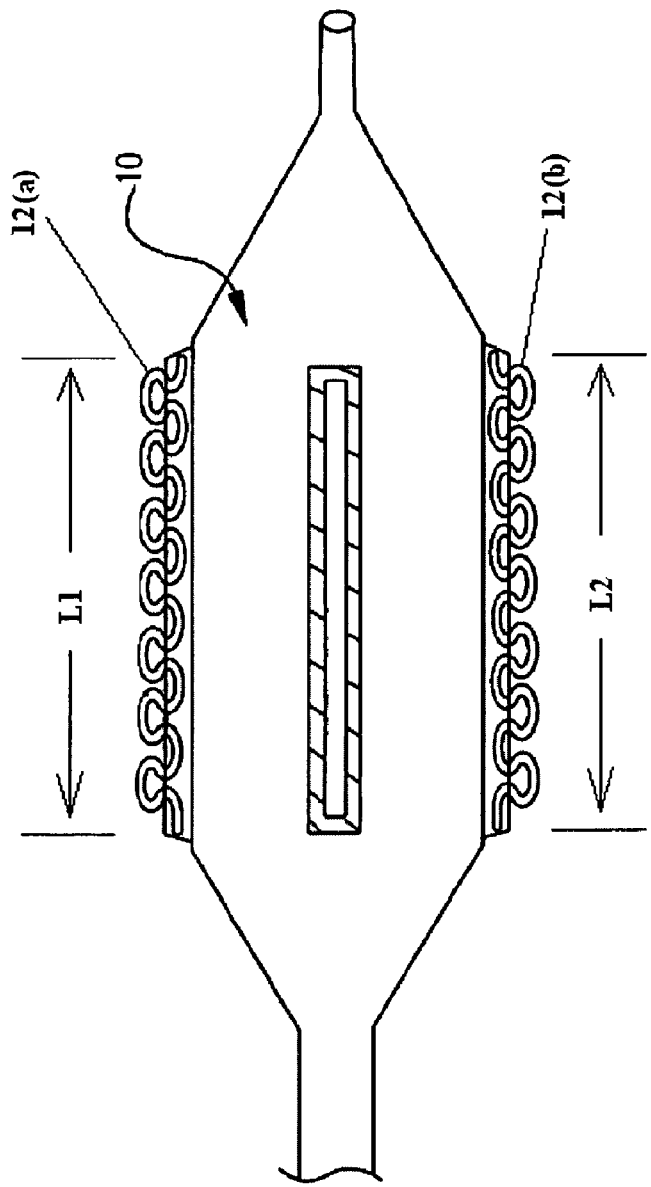
FIG. 14 is a side view of the embodiment shown in FIG. I wherein the serpentine blades are positioned on the body or working portion of the balloon, the serpentine blades having different lengths.

In some embodiments a balloon 10 may be provided with one or more blades having different lengths, sizes, shapes, or configurations. For example, FIG. 14 depicts a balloon 10 having two blades, 12(a) and 12(b), with lengths L1 and L2, respectively, where length L1 is greater than length L2. In at least one embodiment one or more blades on a balloon have a length which extend from at least the body of the balloon and through at least a portion of the balloon waist, while the distal end of the blade terminates before reaching the distal waist. This and other configurations and arrangements of blades should be recognized as falling within the scope of the present invention.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim 1 such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

The invention claimed is:

1. A system for treatment of a vessel lesion comprising:
an expandable balloon including a proximal waist, a proximal cone immediately adjacent to the proximal waist, a distal waist, a distal cone immediately adjacent to the distal waist, and a body, the body extending between the proximal cone and the distal cone; and
at least one cutting blade engaged to an exterior surface of the balloon, the at least one blade comprising a body region extending along at least a portion of the body of the balloon, a distal end region and a proximal end region;
the body portion of the at least one cutting blade having a substantially serpentine configuration defined by a plurality of interconnected peaks and troughs wherein each trough is in closer proximity to the balloon than each peak, the at least one cutting blade having a lower surface facing the body of the balloon that undulates toward the balloon at the troughs and away from the balloon at the peaks;
the at least one cutting blade extending substantially parallel to a longitudinal axis of the balloon.

2. The system of claim 1 wherein the body region comprises the substantially serpentine configuration.

3. The system of claim 1 wherein only each trough of the body region is engaged to the external surface of the balloon body.

4. The system of claim 3 wherein each trough is adhesively engaged to the external surface of the balloon.

5. The system of claim 1 wherein at least each peak of the body region defines a cutting edge.

6. The system of claim 5 wherein the body region of the blade has substantially triangular cross-sectional shape.

7. The system of claim 6 wherein at least one region of the blade adjacent to the body region has a cross-sectional shape different than that of the body region.

8. The system of claim 7 wherein the cross-sectional shape different than that of the body region is selected from at least one member of the group consisting of, substantially round, substantially ovoid, substantially square, substantially rectangular, and any combination thereof.

9. The system of claim 1 wherein the at least one cutting blade includes a proximal transition region between the body region and the proximal end region, and a distal transition region between the body region and the distal end region, wherein at least a portion of the body region has the substantially serpentine configuration, the proximal transition region and the distal transition region do not have the serpentine configuration.

10. The system of claim 9 wherein the proximal transition region and the distal transition region are substantially linear.

11. The system of claim 9 wherein the at least one cutting blade includes a distal cone region extending along at least a portion of the distal cone and a proximal cone region extending along a least a portion of the proximal cone, wherein each cone region has the substantially serpentine configuration.

12. The system of claim 11 wherein the substantially serpentine configuration of the body region defines a wavelength that is shorter than a wavelength of the substantially serpentine configuration of either the proximal cone region or the distal cone region.

13. The system of claim 12 wherein the proximal end region and the distal end region do not have the substantially serpentine configuration.

14. The system of claim 13 wherein the proximal end region and the distal end region are substantially linear.

15. The system of claim 13 wherein the proximal end region is fixedly engaged to at least a portion of the proximal waist and the distal end region is fixedly engaged to at least a portion of the distal waist.

16. The system of claim 13 wherein the proximal end region is fixedly engaged to at least a portion of the catheter shaft adjacent to the proximal waist and the distal end region is fixedly engaged to at least a portion of the catheter shaft adjacent to the distal waist.

17. The system of claim 1 wherein 1 to about 20 cutting blades are engaged to the exterior surface of the balloon.

18. The system of claim 1 wherein there are a plurality of cutting blades distributed symmetrically about the exterior surface of the balloon.

19. The system of claim 1 wherein there are a plurality of cutting blades, and wherein one or more of the plurality of blades engaged to the exterior surface of the balloon have different lengths.

20. The system of claim 1 wherein at least a portion of the at least one blade is radiopaque.

21. The system of claim 1, wherein the system comprises at least one therapeutic agent.

22. The system of claim 1 wherein there are a plurality of cutting blades, and wherein one or more of the plurality of blades engaged to the exterior surface of the balloon are constructed of different materials, the different materials selected from the group consisting of at least one metal, polymer, and combination of at least one metal and polymer.

* * * * *